(12) United States Patent
Sivavec et al.

(10) Patent No.: US 6,357,278 B1
(45) Date of Patent: Mar. 19, 2002

(54) POLYMER COATINGS FOR CHEMICAL SENSORS

(75) Inventors: Timothy Mark Sivavec, Clifton Park; Radislav Alexandrovich Potyrailo, Niskayuna, both of NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/370,135

(22) Filed: Aug. 9, 1999

(51) Int. Cl.$^7$ ................................................ G01N 29/02
(52) U.S. Cl. ........................ 73/24.01; 96/108; 96/154; 252/408.1; 310/313 A; 442/69; 442/88; 428/447; 428/482
(58) Field of Search .................. 73/24.01; 422/69, 422/88; 428/447, 428, 482; 525/430, 431, 449, 446; 310/313 A; 96/108, 154; 252/408.1

(56) References Cited

U.S. PATENT DOCUMENTS

| | | | |
|---|---|---|---|
| 4,759,210 A | | 7/1988 | Wohltjen |
| 4,994,532 A | * | 2/1991 | Hawkins et al. |
| 5,209,981 A | * | 5/1993 | Rojstaczer |
| 5,703,161 A | * | 12/1997 | Steenblock et al. |
| 5,738,158 A | * | 4/1998 | Ozawa et al. |
| 5,756,631 A | | 5/1998 | Grate |
| 5,880,552 A | * | 3/1999 | McGill et al. |
| 5,900,471 A | * | 5/1999 | Glans |
| 6,056,805 A | * | 5/2000 | Litwin et al. |

FOREIGN PATENT DOCUMENTS

JP 08-311233 A * 11/1996

OTHER PUBLICATIONS

American Chemical Society (1994), Stephen J. Martin & Gregory C. Frye, Dynamics and Response of Polymer–Coated Surface Acoustic Wave Devices: Effect of Viscoelastic Properties and Film Resonance, pp. 2201–2218.

Analytical Chemistry (Mar. 15, 1995), Edward T. Zellers, Stuart A. Batterman, Mingwei Han and Samuel J. Patrash. Optimal Coating Selection for the Analysis of Organic Vapor Mixtures with Polymer–Coated Surface Acoustic Wave Sensor Arrays, pp. 1092–1106.

Sensors and Actuators B, 3 (1991), Jay W. Grate, Review Paper, Solubility interactions and the design of chemically selective sorbent coatings for chemical sensors and arrays, pp. 85–111.

Silicones in Coatings II, Mar. 24, 1998, A Technology Forum Exploring the Versatility of Silicone, The Design of Aromatic Acid Silicone Polymers and Their Evaluation as Sorbent Coatings for Chemical Sensors Paper 3.

Journal Of Applied Polymer Science (1991), vol. 43, A. W. Snow, L. G. Sprague, R. L. Soulen, J. W. Grate and H. Wohltjen, Synthesis and Evaluation of Hexafluorodimethylcarbinol Functionalized Polymers as Microsensor Coatings, pp. 1659–1671.

Handbook of Biosensors and Electronic Noses, Medicine, Food and the Environment (1997), Jay W. Grate, Michael H. Abraham and R. Andrew McGill, Sorbent Polymer Materials for Chemical Sensors Arrays, pp. 593–612.

American Chemical Society (1992), Jay W. Grate and Mark Klusty, The Predominant role of Swelling–Induced Modulus Changes of the Sorbent Phase in Determining the Responses of Polymer–Coated Surface Acoustic Wave Vapor Sensors, pp. 610–624.

* cited by examiner

Primary Examiner—Robert E. L. Sellers
Assistant Examiner—Marc S. Zimmer
(74) Attorney, Agent, or Firm—Toan P. Vo; Noreen C. Johnson

(57) ABSTRACT

A sensor comprises a substrate and a polymeric film disposed on the substrate. The polymeric film comprises at least one hardblock component and at least one softblock component. The invention also sets forth a method for enhancing detection of a target compound by a sensor. The method comprises disposing a polymeric film on a surface of the sensor, in which the polymeric film enhances detection of target compounds not normally sensed by a sensor without the polymeric film. The polymeric film comprises at least one hardblock component and at least one softblock component.

37 Claims, 10 Drawing Sheets

POLYMER COATINGS FOR CHEMICAL SENSORS

BACKGROUND OF THE INVENTION

This invention relates to use of polymeric films in sensors.

Mass-sensitive sensors have varying configurations. Typically, a sensor is provided with a chemically sensitive film that is applied onto a surface of the sensor, for example onto the surface of the sensor's crystal. Interactions of the film with a material to be detected, for example an analyte, induce a change in at least one of the mass and visco-elastic properties of the film. This change is measured as a shift of the resonance frequency of the sensor's crystal and is related to the concentration of the analyte. For detection of analytes of differing nature, the coating and analyte interactions include, but are not limited to, hydrogen bonding, π-stacking, acid-base, electrostatic and size/shape recognition.

The sensor's configuration, materials, and other characteristics vary to define operational characteristics, resonance frequencies, and boundaries for the sensor. For example, differing piezoelectric materials for a sensor substrate operate differently, and thus define the sensor's operational boundaries and characteristics. Therefore, if a sensor comprises a quartz crystal microbalance (QCM) as a sensor substrate, the sensor operates by propagating mechanical oscillations generally perpendicularly between parallel faces of a thin, quartz-crystal piezoelectric element. If a sensor comprises a surface acoustic wave (SAW) device as a sensor substrate, mechanical oscillations are propagated in substantially up-and-down undulations at a radio frequency (RF) along the surface of a thin, quartz-crystal piezoelectric element.

The chemically sensitive film permits the sensor to more readily detect a target analyte or other compound (hereinafter "target compound"), which is not ordinarily sensed by the sensor. The sensitive film often comprises a polymeric material film (hereinafter "polymeric film"), which changes the response of the sensor by altering the sensor's mechanical oscillation frequencies, and thus permitting the target compound to be detected by the sensor. The sensor's changing frequencies result from the polymeric film's interaction with the target compound. Accordingly, various target compounds can be detected by a sensor when the nature of reaction between the polymeric film and target compound is known.

The target compound, usually a vapor, is dissolved (absorbed) into the film, by a process known in the art as "partitioning." A partition coefficient, K, is a thermodynamic parameter that corresponds to an equilibrium distribution of sorbed molecules between the gas phase and polymeric film. The partition coefficient is ratio of a concentration of target compound in the polymeric film, $C_F$, to the concentration of the target compound outside of the film, $C_V$. The partition coefficient K is determined according to Equation (1)

$$K = C_F/C_V \qquad \text{(Equation 1)}$$

One example of such an altered frequency results from a changed polymeric film mass. An increased film mass lowers a frequency at which the crystal oscillates, including for which it oscillates when exposed to a target compound. Thus, the target compound perturbs the oscillation of the sensor when the mass of the polymeric film increases, and thus the target compound can be detected. The oscillation frequency and mass change of a polymeric film often necessitate that it be thin and mechanically rigid. The thin nature of a polymeric film is needed so that the polymeric film's visco-elastic properties, and any changes in those visco-elastic properties produced by partitioning of the target compound thereto, do not adversely influence the oscillations of the sensor and provide inaccurate detection of a target compound. Further, the polymeric film should be mechanically rigid so the sensor provided with the polymeric film can have repeated sensing applications.

SAW sensor devices coated with thin polymeric material film (known in the art as "chemosensors") have been used as micro-sensors for detecting vapors. The sensitivity to a specific vapor (target compound) for such a SAW chemosensor depends on the type, physical and chemical properties, and materials of polymeric film. For example, each of a polymer-vapor partition coefficient, rate of absorption, and desorption processes influence the operational characteristics of a polymeric film. Examples of materials for polymeric films used as on a SAW chemosensor include, but are not limited to, phenyl-methyl-polysiloxanes, poly(epichlorohydrin), poly(isobutylene), poly(ethylene maleate), and poly(ethylenimine). Some of these materials do not provide stable operations in which controlled, accurate, reliable, and repeated detections are possible. Although SAW sensors are more sensitive than QCM sensors, the relatively low partition coefficients of polymers used in the past preclude the use of SAW and QCM sensors for detection of low concentrations of analytes.

A sensor with polymeric film that provides capabilities for determination of low concentrations of analytes (also known as target compounds) is needed. The polymeric film should also provide a long term stability of operation for reliable detection results.

SUMMARY OF THE INVENTION

A sensor comprises a substrate and a polymeric film disposed on the substrate. The polymeric film comprises at least one hardblock component and at least one softblock component.

The invention also sets forth a method for enhancing detection of a target compound by a sensor. The method comprises disposing a polymeric film on a surface of the sensor, in which the polymeric film enhances detection of target compounds not normally sensed by a sensor without the polymeric film. The polymeric film comprises at least one hardblock component and at least one softblock component.

A polymeric film for a sensor is further set forth by the invention. The polymeric film comprises at least one hardblock component and at least one softblock component.

These and other aspects, advantages and salient features of the invention will become apparent from the following detailed description, which, when taken in conjunction with the annexed drawings, where like parts are designated by like reference characters throughout the drawings, disclose embodiments of the invention.

DESCRIPTION OF THE INVENTION

Figure 1:
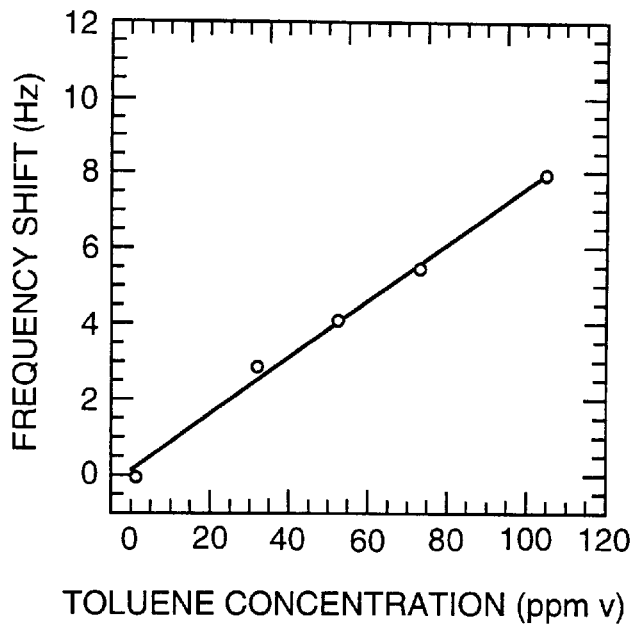
FIG. 1 is a calibration curve for the determination of toluene with polymer-coated QCM sensors at 20° C. with a polymeric film comprising BPA-PC-Silicone 81% DMS "BPASI"
Figure 2:
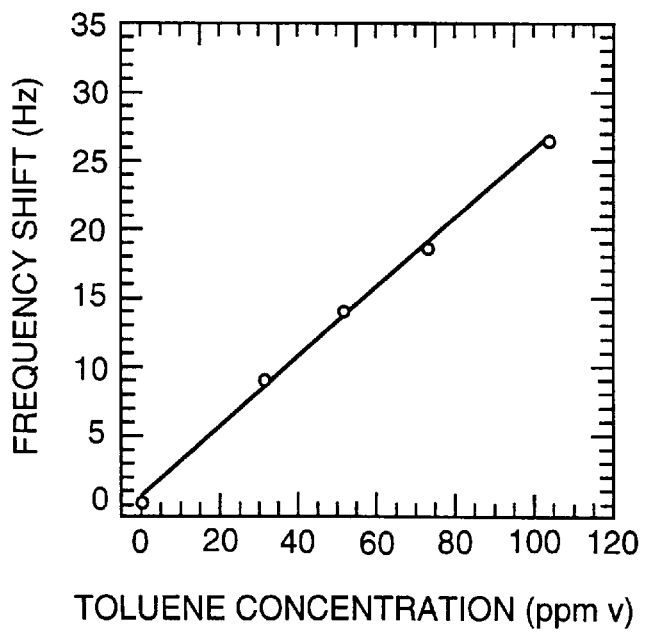
FIG. 2 is a calibration curve for the determination of toluene with polymer-coated QCM sensors at 20° C. with a polymeric film comprising BPA-PC-Silicone 50% DMS "XD-7"
Figure 3:
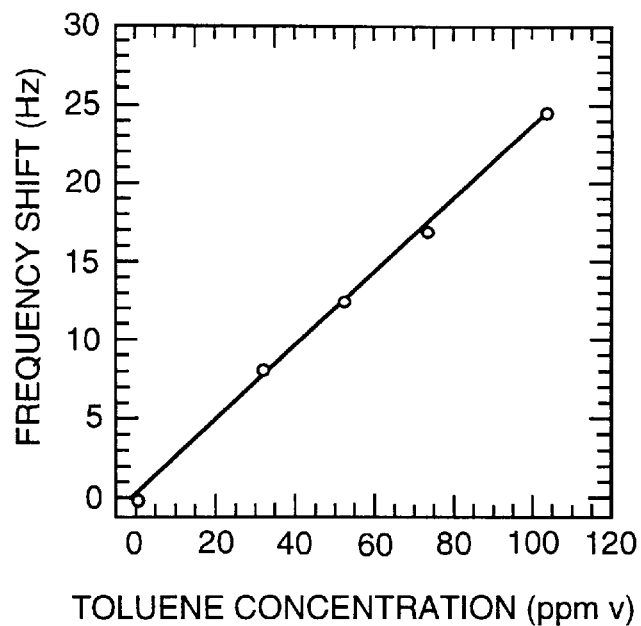
FIG. 3 is a calibration curve for the determination of toluene with polymer-coated QCM sensors at 20° C. with a polymeric film comprising Hytrel 3078.
Figure 4:
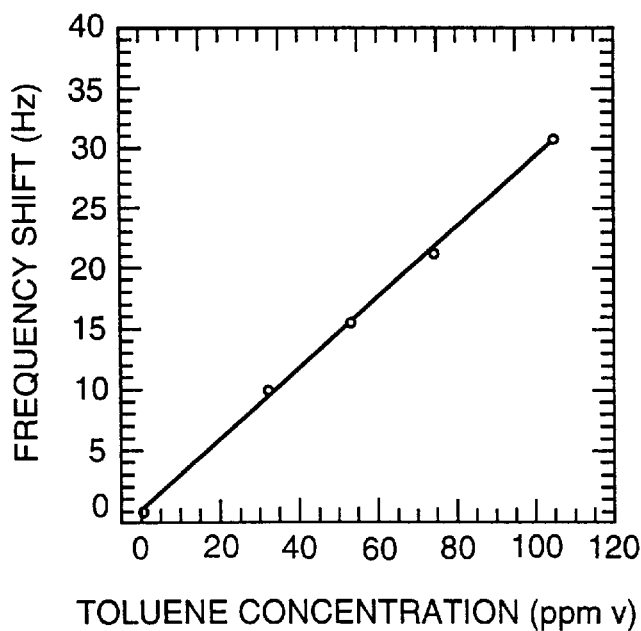
FIG. 4 is a calibration curve for the determination of toluene with polymer-coated QCM sensors at 20° C. with a polymeric film comprising Lomod J613.
Figure 5:
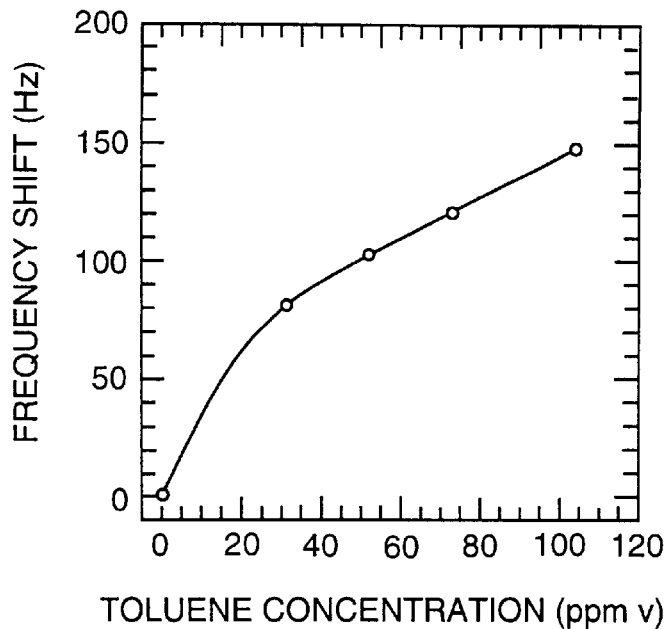
FIG. 5 is a calibration curve for the determination of toluene with polymer-coated QCM sensors at 20° C. with a polymeric film comprising Siltem 2000.
Figure 10:
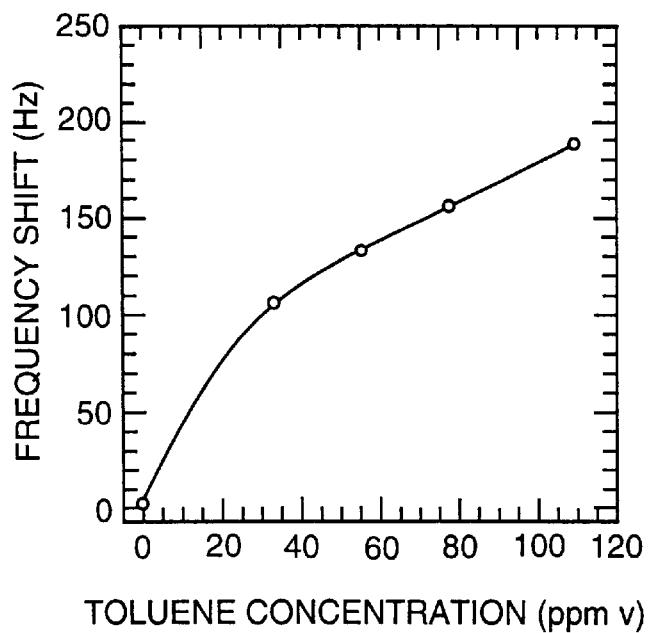
FIG. 10 is a calibration curve for the determination of TCE with polymer-coated QCM sensors at 20° C. with a polymeric film comprising Siltem 2000.
Figure 6:
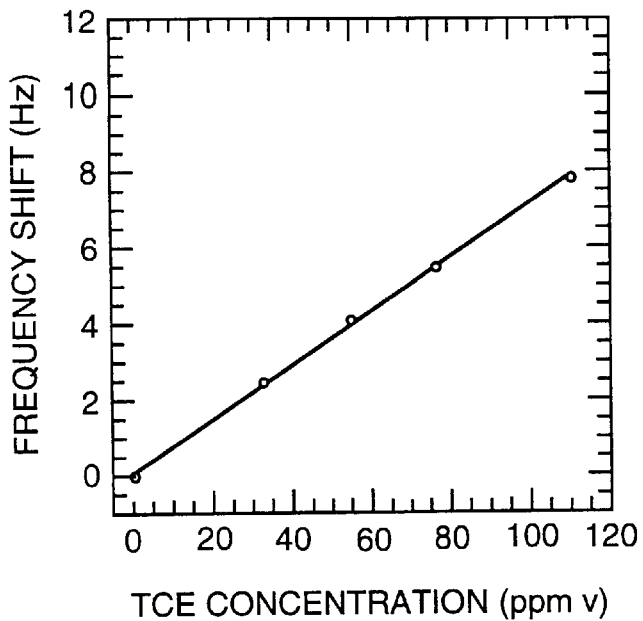
FIG. 6 is a calibration curve for the determination of TCE with polymer-coated QCM sensors at 20° C. with a polymeric film comprising BPA-PC-Silicone 81% DMS "BPASI"
Figure 7:
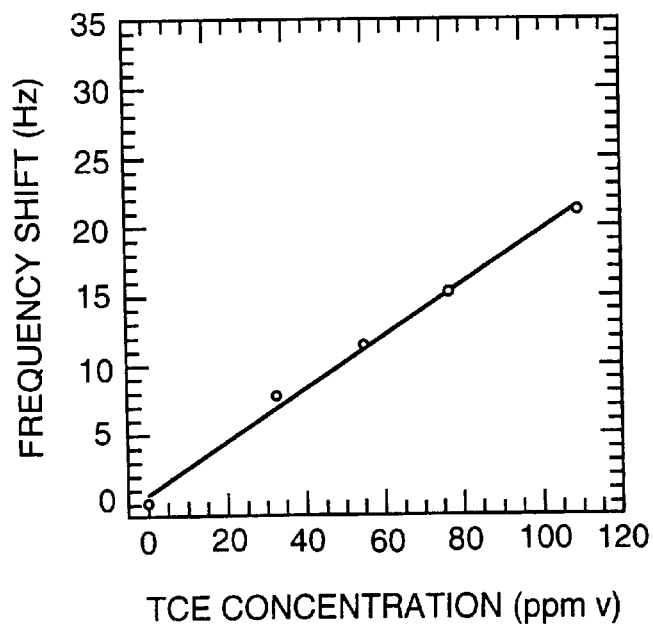
FIG. 7 is a calibration curve for the determination of TCE with polymer-coated QCM sensors at 20° C. with a polymeric film comprising BPA-PC-Silicone 50% DMS "XD-7"
Figure 8:
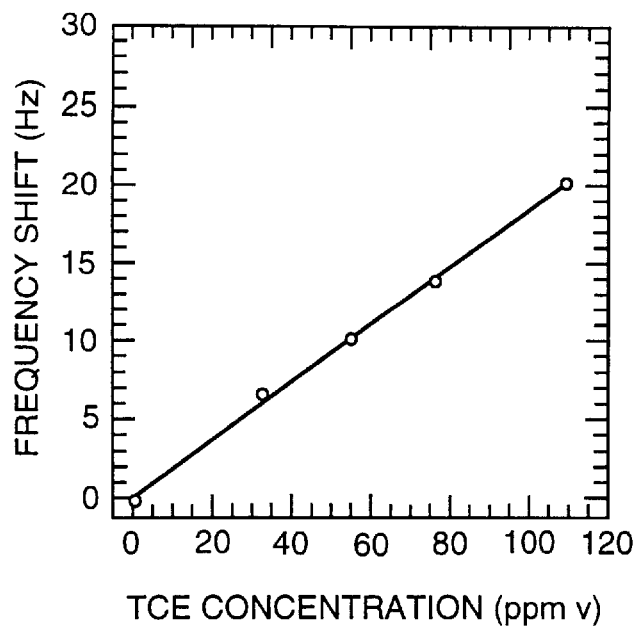
FIG. 8 is a calibration curve for the determination of TCE with polymer-coated QCM sensors at 20° C. with a polymeric film comprising Hytrel 3078.
Figure 9:
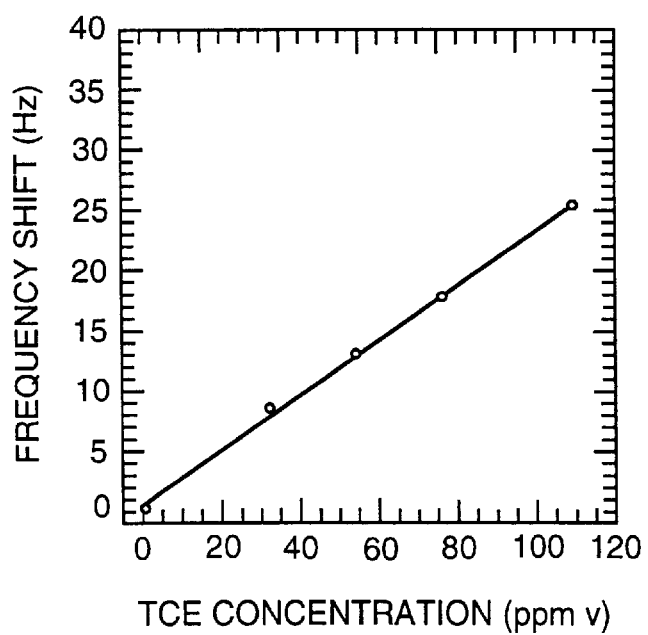
FIG. 9 is a calibration curve for the determination of TCE with polymer-coated QCM sensors at 20° C. with a polymeric film comprising Lomod J613.

Sensors, as embodied by the invention, comprise polymeric films disposed on a surface of the sensor, in which the sensor is used to detect a target compound. The polymeric films, as embodied by the invention, comprise polymers that include hardblock and softblock polymers, such as thermoplastic elastomers. The polymeric film is disposed as a polymeric film coating on a surface of a sensor's piezoelectric crystal, and can be applied by accepted coating techniques.

A sensor, as embodied by the invention, comprises any appropriate sensor and sensor substrate, such as, but not limited to, acoustic wave sensors that include but are not limited to, quartz crystal microbalance (QCM) sensors, and surface acoustic wave (SAW) chemical sensors. These sensors are chemical sensors and find use in many diverse detection applications. The applications include monitoring in which it is desirable to detect various target compounds.

A polymeric film provides a sensor with an enhanced ability to detect some target compounds, for example hydrocarbon and chlorinated hydrocarbon vapors. These target compounds are not typically detected by certain sensors because they result in no or undetectable oscillations in the sensor, as these sensors typically function in the gravimetric range, meaning that the sensor's response in essentially mass sensitive. The enhanced ability to detect some target compounds is believed to be due, at least in part, to increased polymer-vapor affinity between the target compound and the sensor equipped with the polymeric film. The enhanced polymer-vapor affinity results in an increased measurement sensitivity. The enhanced measurement sensitivity for changed oscillation frequencies is typically about 1 part in about $10^8$. Therefore, measurement sensitivities for oscillation frequencies are not significantly affected by plasticization and associated visco-elasticity variation of the polymeric film.

The polymeric films, which include hardblock and softblock polymer base structures, exhibit reduced swelling and plasticization, compared to known films, upon exposure to target compounds, including, but not limited to, hydrocarbon and chlorinated hydrocarbon vapors. Accordingly, a sensor provided with a polymeric film does not exhibit the swelling of prior polymeric film-equipped sensors.

The polymeric film comprises at least one polymer selected from polyester elastomer, polyether block polyamides, silicone polyimides, and combinations thereof. Each of these polymers includes, but is not limited to, softblock and hardblock components. Polymers that comprises a hardblock and softblock base structure comprise repeating high-melting blocks that are the hardblock components capable of crystallization, and amorphous softblock components that possess a relatively low glass transition temperature. Examples of hardblock and softblock polymeric materials are set forth in U.S. Pat. Nos. 5,595,586 and 5,391,300, the entire contents of which are incorporated herein by reference. U.S. Pat. No. 5,595,586 teaches a method to sorb and desorb volatile organic compounds (VOCs), such as trichloroethylene (TCE), from air using softblock and hardblock polymers.

The hardblock and softblock components of the polymeric film partition the target compound into the polymeric film, for example hydrocarbon vapor, as it enters the polymeric film. The hardblock and softblock components of the polymeric film are believed to provide structural integrity to the polymeric film. The hardblock and softblock components are also believed to reduce swelling of the polymeric films' polymer and its associated effects, when the polymeric film is exposed to hydrocarbon vapors. Further, the hardblock and softblock components are believed to enhance surface adhesion of the polymeric film to a surface of the sensor's piezoelectric crystal. The enhanced surface adhesion is desirable for extended sensor life for repeated absorption and desorption cycle applications.

One polymeric film, which includes a polyester elastomer, comprises hardblock and softblock components. An exemplary softblock component comprises polyoxyalkylene diimide diacids, and an exemplary hardblock component comprises polyalkylene terephthalate. These materials are commercially available as HYTREL™ resins from DuPont and LOMOD™ resins from General Electric Company.

Another polymeric film, as embodied by the invention, comprises polyether block polyamides. The polyether block polyamides comprise polyether softblock components and polyamide (nylon hardblock) components. These materials are commercially available from Atochem, Inc. as PEBAX™ resins.

A further polymeric film, as embodied by the invention, comprises silicone polyimides (sometimes referred to as "silicone polyetherimides"). Silicone polyimides are known in the art and are described, for example, in U.S. Pat. Nos. 4,808,686 and 4,690,997; the entire contents of which are incorporated herein as reference.

An example of a polymeric film on a sensor, as embodied by the invention, will now be discussed. A quartz crystal microbalance (QCM) sensor is provided with an AT-cut quartz crystal as a sensor substrate with gold (Au) electrodes. The crystal typically oscillates in a thickness-shear mode with a fundamental frequency of about 10 MHz. A polymeric film, as embodied by the invention, is disposed on a surface of the sensor. The film is disposed by appropriate processes, including but not limited to, is achieved by dip coating, spin coating, spray coating, vapor deposition, laser-assisted deposition, and other known methods.

The sensor will exhibit a changed oscillation frequency due to mass changes when contacted with material, for example a vapor, that includes the target compound. The mass increase of the sensor and the quartz crystal occurs through a solubility interaction between the polymeric film and vapor, which includes the target compound. This interaction produces a frequency shift (or change) of oscillations at the resonance frequency. Therefore, the change in oscillation frequency that is attributed to the target compound can be accurately detected.

Polymeric films, as embodied by the invention, comprise sorbent materials. The sorbent materials, as embodied by the invention, comprise polymers with a single or several closely related repeating structural units. The repeating structural units are functionalized with groups to enhance selectivity and sensitivity of the sensor sorb target compounds. Using appropriate repeating structural units that are functionalized with appropriate groups, different target compounds can be detected. A glass transition temperature of the sorbent materials is lower and higher than operating temperatures for the first (soft) and the second (hard) structural polymer units, respectively. Further, different repeating structural units that are functionalized with such groups can be used in sensor arrays, so as to detect a plurality of target compounds.

The partition coefficient K is described above. The partition coefficient K thermodynamic parameter corresponds to an equilibrium distribution of sorbed molecules between the gas phase and polymeric film. The partition coefficient K is determined by Equation (1). A larger partition coefficient corresponds to an enhanced signal change for a sensor. The partition coefficient is determined in accordance with Equation (1):

$$K = C_F/C_V \quad \text{(Equation 1)}$$

where $C_F$ is a concentration of target compound in the polymeric film and $C_V$ is the concentration of a target compound outside of the film.

If a density of the film $\rho_F$, a change in resonant frequency upon film deposition $Df_F$, a concentration of the target compound C in the vapor, and a partition coefficient K of the film are known, a response for a acoustic wave sensor $\Delta f_v$ can be determined in accordance with Equation (2):

$$\Delta f_v = (\Delta f_F C_v K)/\rho_F \quad \text{Equation (2)}$$

Materials used as polymeric films, as embodied by the invention, are listed in Table 1. The Table also lists a reference material, polyisobutylene, that provides an indication of the effectiveness of polymeric films, as embodied by the invention. Table 1 also lists logs of partition coefficients (K) for these polymeric films for toluene ($K_{toluene}$) and TCE ($K_{TCE}$). Partition coefficients are presented as mean±SD (standard deviation) for n=4 (number of observations), for the concentration range from 32 to 105 parts per million in the vapor phase (ppmv) of toluene and from 33 to 110 ppmv of TCE, except for the values marked with an asterisk (*) which are presented for 0.1 ppmv of TCE.

Materials listed in Table 1 used for fabrication of polymeric films on the QCM sensors for quantification of varying concentrations of toluene and TCE. Calibration curves for these polymeric films on sensors are presented in FIGS. 1–10. All calibration curves with the polymeric films are generally linear over the investigated concentration range of analytes, with the exception of Siltem materials.

Figure 11:
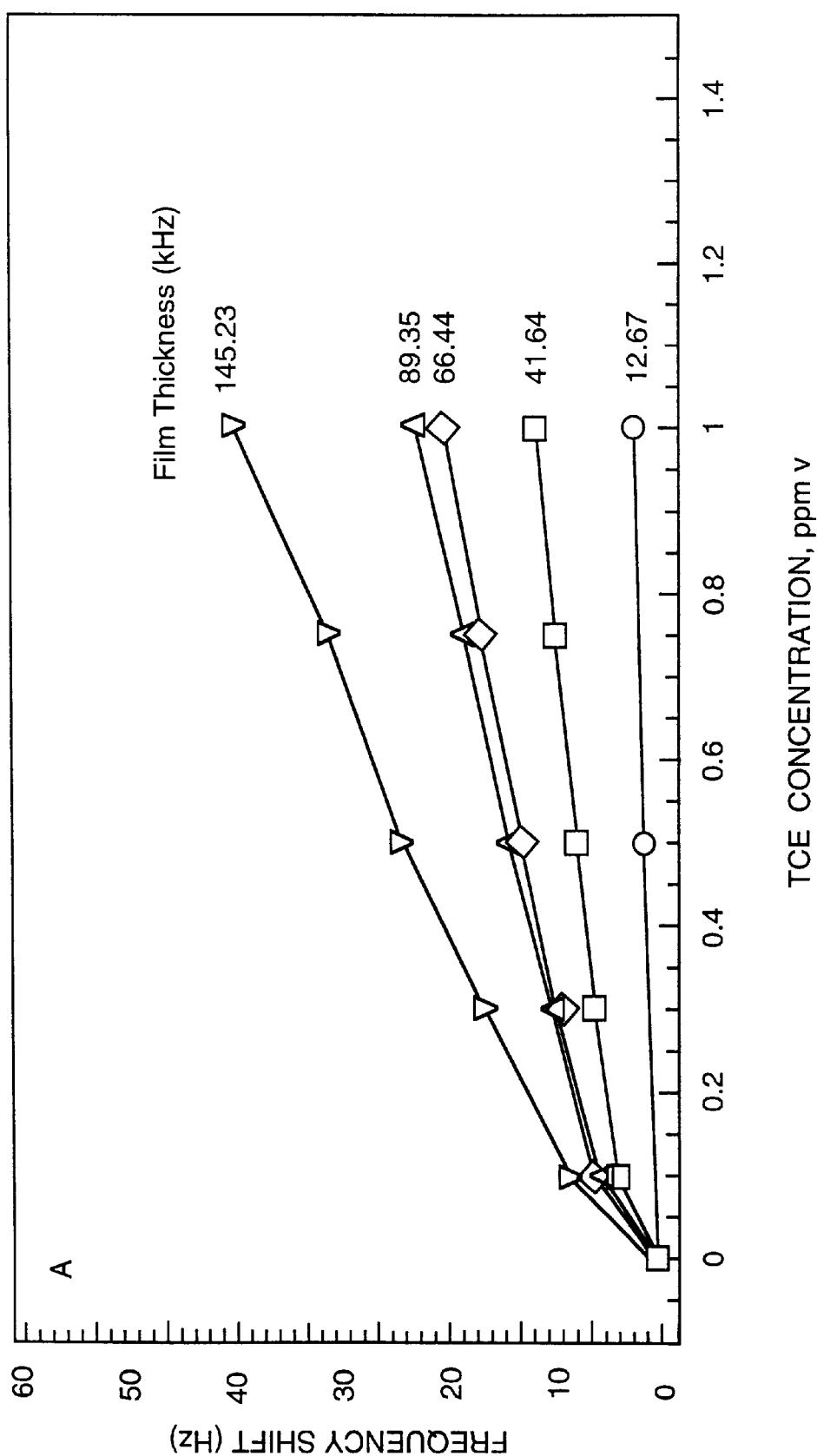
FIG. 11 is a calibration curve for the determination of sub-ppmv levels of TCE with QCM sensors at 20° C. coated with Siltem 2000 polymer films of different thickness, as indicated.
Figure 12:
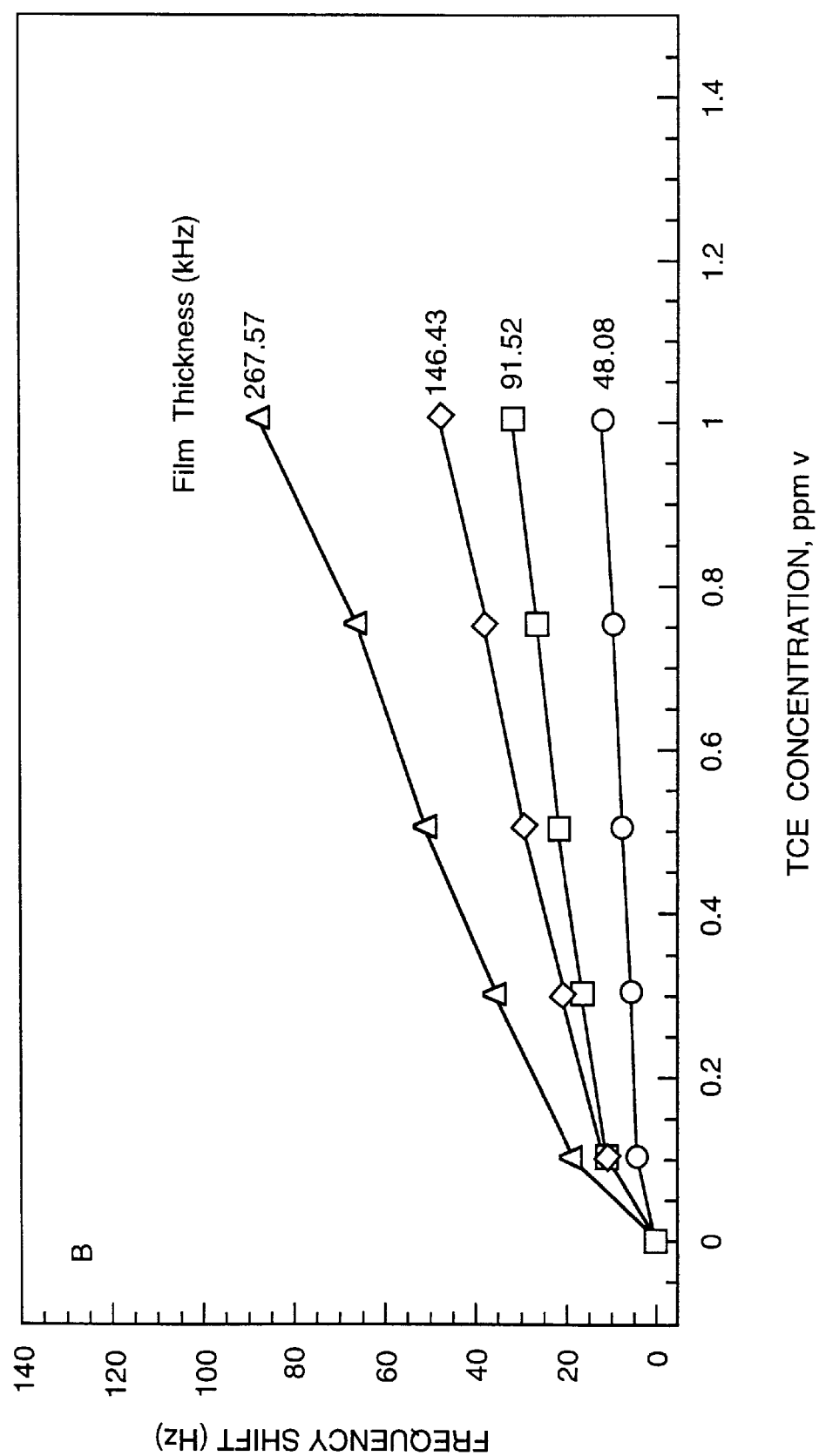
FIG. 12 is a calibration curve for the determination of sub-ppmv levels of TCE with QCM sensors at 20° C. coated with Siltem G15/40 polymer films of different thickness, as indicated.
Figure 13:
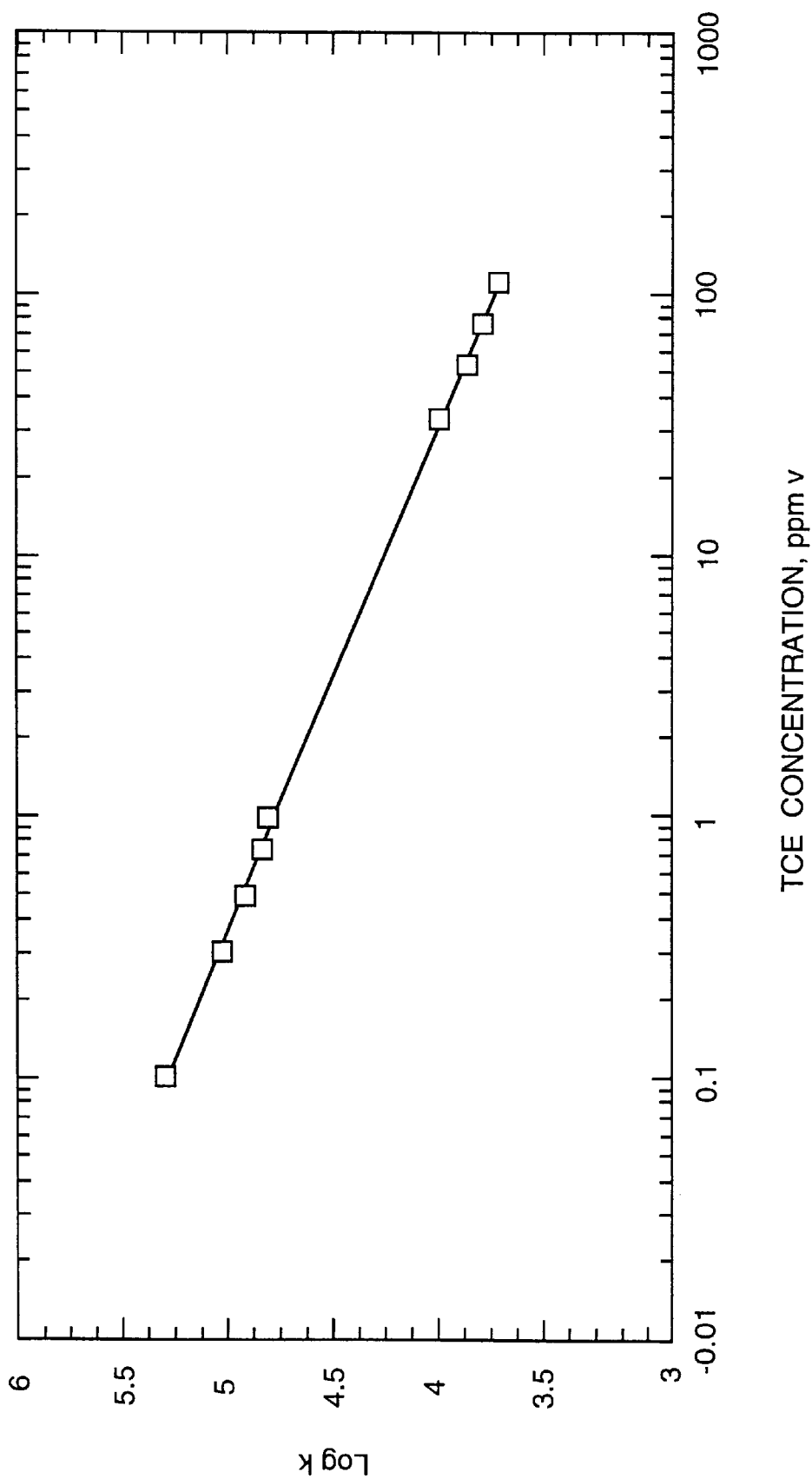
FIG. 13 is a graph of log K, partition coefficient, of Siltem 2000 coated chemical sensors as a function of TCE concentration.

Trace levels of target compounds (analytes) can be detected with Siltem materials. For example, calibration curves for determination of sub-ppmv levels of TCE with QCM sensors at 20° C. coated with polymers of different thickness are presented in FIGS. 11 and 12. This capability is achieved due to the drastically enhanced partition coefficient of Siltem materials for low analyte concentrations. FIG. 13 illustrates a logarithmic dependence of the partition coefficients of Siltem on concentration of TCE vapor. Similar dependence is observed for toluene.

Figure 14:
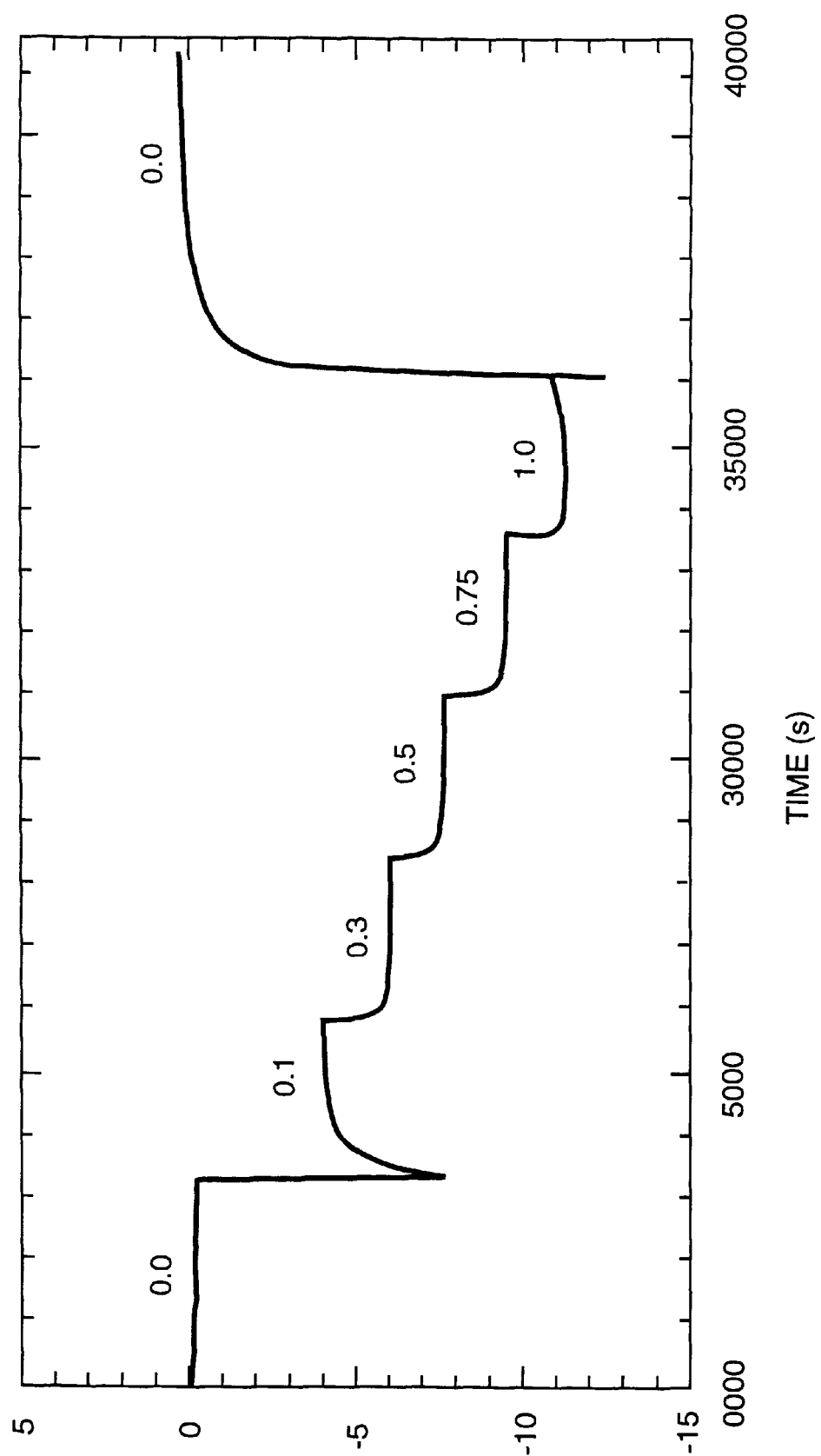
FIG. 14 is a graph illustrating the dynamic response of Siltem-coated chemical sensors, Siltem 2000 film thickness 41 kHz, to step changes in TCE concentration at 20° C., in which the numbers on the graph indicate TCE concentrations in ppmv at each step.
Figure 15:
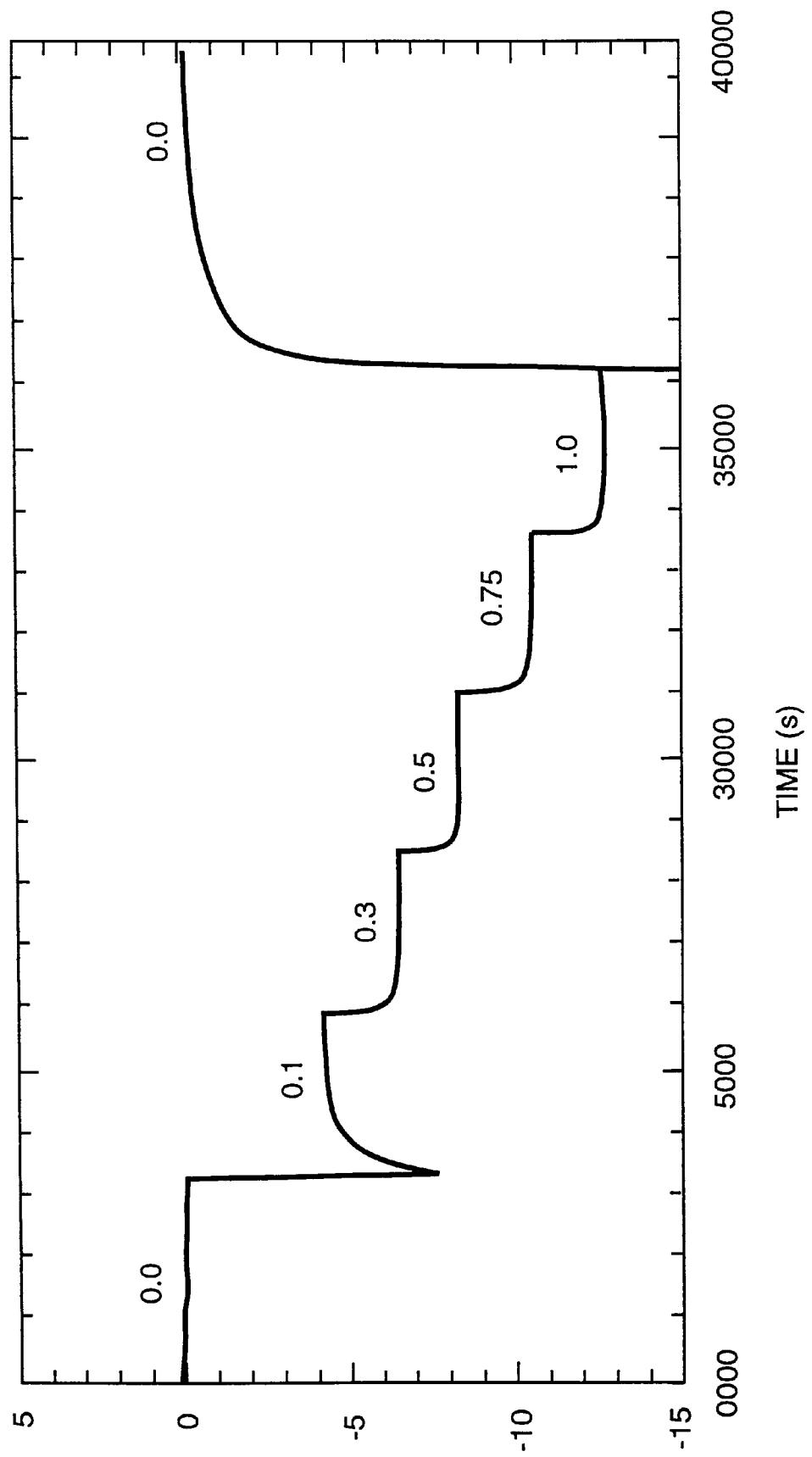
FIG. 15 is a graph illustrating the dynamic response of Siltem-coated chemical sensors, Siltem G15/40 film thickness 48 kHz, to step changes in TCE concentration at 20° C., in which the numbers on the graph indicate TCE concentrations in ppmv at each step.

The materials, as embodied by the invention, when applied as polymeric films for chemical sensors, provide a reversible sensor response upon sequential exposure of coated sensors to analyte vapors and blank gas. A reversible sensor response means that the ability of the sensor is able to return to an original value, as illustrated about a 0.0 TCE concentration after a certain number of runs or after a certain temperature has been reached. FIGS. 14 and 15 illustrate the reversible response of polymer-coated QCMs to step changes in trichloroethylene concentrations in nitrogen.

TABLE 1

| Material | log ($K_{toluene}$) | log ($K_{TCE}$) |
|---|---|---|
| BPA-PC-Silicone 81% DMS "BPASI" | 2.95 ± 0.04 | 2.76 ± 0.01 |
| BPA-PC-Silicone 81% DMS "IXD-7" | 3.32 ± 0.03 | 3.07 ± 0.04 |
| Hytrel ™ 3078 | 3.35 ± 0.02 | 3.09 ± 0.02 |
| Lomod ™ J613 | 3.28 ± 0.02 | 3.03 ± 0.02 |
| Siltem ™ | 4.0 ± 0.1 | 3.9 ± 0.1 |
|  |  | 5.33 ± .06* |
| Siltem ™ | — | 5.44 ± .03* |
| Polyisobutylene** | 3.08 ± 0.02 | 2.76 ± 0.03 |

**reference material.

The following are chemical formulae for the materials used as polymeric films, as embodied by the invention.

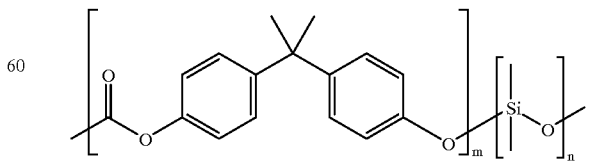

wherein m is from 1 to about 4, and n is from about 3 to about 20;

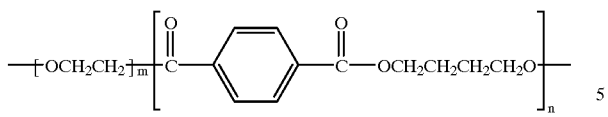

wherein m is from about 10 to about 300, and n is from about 5 to about 300;

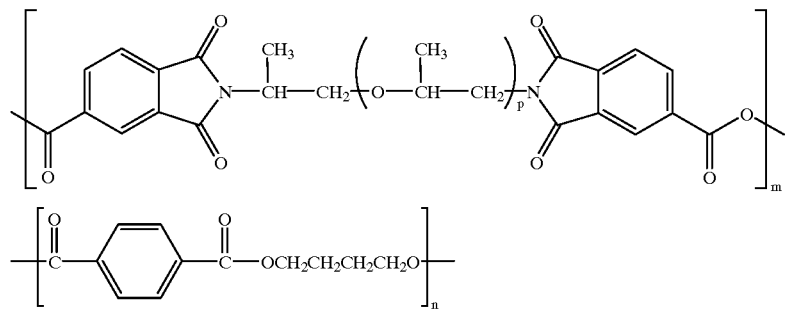

where m from 1 to about 60, p is from about 10 to about 200, and n is from about 5 to about 300; and

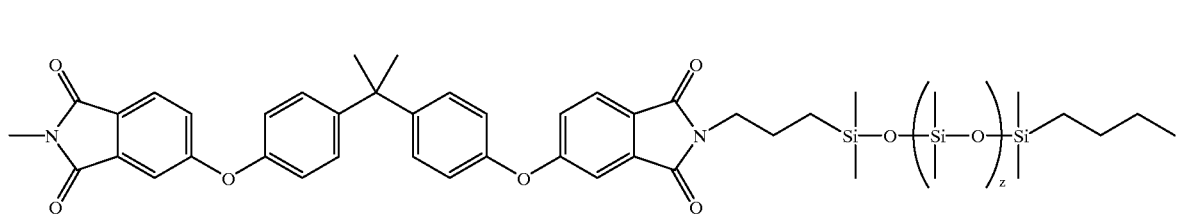

where x is from 1 to about 60, y is from about 40 to about 65, and z is from about 3 to about 20.

While various embodiments are described herein, it will be appreciated from the specification that various combinations of elements, variations or improvements therein may be made by those skilled in the art, and are within the scope of the invention.

What is claimed is:

1. A chemical sensor for detecting a quantity of a chemical, the chemical sensor comprising:
    a sensor element producing a measurable signal when activated; and
    a polymeric film disposed on a surface of the sensor element, the polymeric film comprising at least one hardblock component and at least one softblock component, the polymeric film being capable of capturing a portion of the quantity of the chemical and inducing a measurable change in the signal, the change in the signal being relatable to the quantity of the chemical adjacent to the sensor element.

2. A sensor according to claim 1, wherein the polymeric film comprises thermoplastic elastomers.

3. A sensor according to claim 1, wherein the sensor comprises a sensor selected from acoustic wave sensors, quartz crystal microbalance (QCM) sensors, or surface acoustic wave (SAW) chemical sensors.

4. A chemical sensor for detecting a quantity of a chemical, the chemical sensor comprising:
    a sensor element producing a measurable signal when activated; and
    a polymeric film disposed on the sensor element, the polymeric film comprising at least one hardblock component and at least one softblock component, the polymeric film being capable of capturing a portion of the quantity of the chemical and inducing a measurable change in the signal, the change in the signal being relatable to the quantity of the chemical adjacent to the sensor element, wherein the polymeric film comprises at least one polymer selected from polyester elastomer, polyether block polyamides, silicone polyimides, and combinations thereof.

5. A sensor according to claim 1, wherein the polymeric film comprises a component that absorbs hydrocarbon vapor to a degree defined by a partition coefficient of the polymeric component with respect to the hydrocarbon vapor.

6. A sensor according to claim 1, wherein the polymeric film comprises a component that provides at least one of: structural integrity in the polymeric film; reduced swelling of the polymeric films when the polymeric film is exposed to hydrocarbon vapors; and enhanced surface adhesion of the polymeric film to a surface of the sensor.

7. A sensor according to claim 4, wherein the polymeric film comprises polyester elastomer, the polyester elastomer comprising the softblock component and the hardblock component.

8. A sensor according to claim 7, wherein the softblock component comprises polyoxyalkylene diimide diacids and the hardblock component comprises polyalkylene terephthalate.

9. A sensor according to claim 4, wherein the polymeric film comprises polyether block polyamides.

10. A sensor according to claim 9, wherein the polyether block polyamides comprise softblock polyether components and hardblock polyamide (nylon) components.

11. A sensor according to claim 4, wherein the polymeric film comprises silicone polyimides, the silicone polyimides comprising hardblock and softblock elastomers.

12. A sensor according to claim 1, wherein the polymeric film comprises polymers comprising at least one repeating structural units, the repeating structural units being functionalized with groups that enhance selectivity and sensitivity of the sensor to various target compounds.

13. A sensor according to claim 4, wherein the polymeric film comprises:

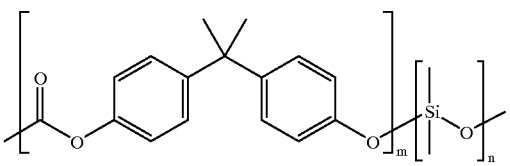

wherein m is in arrange from about 1 to about 4 and n is from about 3 to about 20.

14. A sensor according to claim 4, wherein the polymeric film comprises:

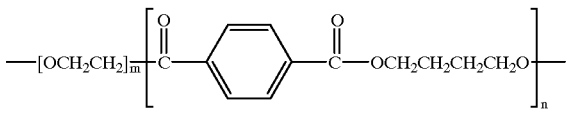

wherein m is in a range from about 10 to about 300 and n is in a range from about 5 to about 300.

15. A sensor according to claim 4, wherein the polymeric film comprises:

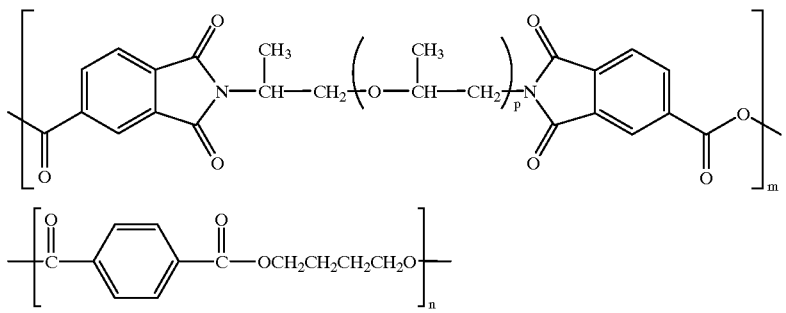

wherein m is in a range from about 1 to about 60, p is in a range from about 10 to 200, and n is in a range from about 5 to about 300.

16. A sensor according to claim 4, wherein the polymeric film comprises:

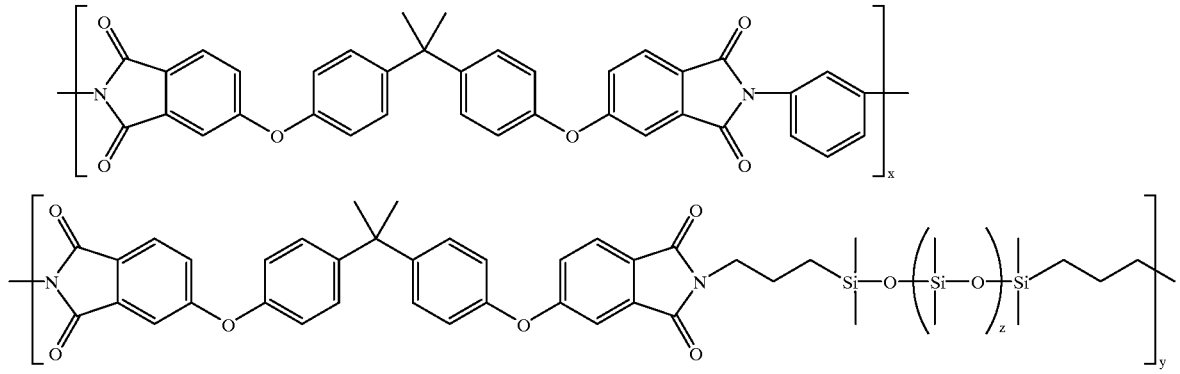

wherein x is in a range from about 1 to about 60, y is in a range from about 40 to 65, and z is in a range from about 3 to about 20.

17. The chemical sensor according to claim 1, wherein the sensor element comprises a piezoelectric substrate.

18. The chemical sensor according to claim 1, wherein the signal is an oscillation frequency.

19. A chemical sensor for detecting a quantity of a chemical, the chemical sensor comprising:
   a sensor element producing a measurable signal when activated; and
   a polymeric film disposed on the sensor element, the polymeric film comprising at least one hardblock component and at least one softblock component, the polymeric film being capable of capturing a portion of the quantity of the chemical and inducing a measurable change in the signal, the change in the signal being relatable to the quantity of the chemical adjacent to the sensor element; wherein the sensor element comprises a quartz crystal microbalance (QCM) sensor that comprises an AT-cut quartz crystal substrate with gold (Au) electrodes.

20. A method for enhancing detection of a target compound by a sensor, the method comprising:
   providing a sensor having a sensor element that produces a characteristic response when activated;
   disposing a polymeric film on a surface of the sensor element, the polymeric film being able to capture a quantity of the target compound and producing a change in the characteristic response of the sensor element as a result of the capture of the target compound, wherein the polymeric film comprises at least one hardblock component and at least one softblock component; and
   relating the change in the characteristic response of the sensor element to a quantity of the target compound adjacent to the sensor element.

21. A method according to claim 20, wherein the polymeric film comprises thermoplastic elastomers.

22. A method according to claim 20, wherein the sensor comprises sensor selected from acoustic wave sensors, quartz crystal microbalance (QCM) sensors, or surface acoustic wave (SAW) chemical sensors.

23. A method according to claim 20, wherein the polymeric film comprises a component that absorbs hydrocarbon vapor to a degree defined by a partition coefficient of the polymeric component with respect to the hydrocarbon vapor.

24. A method according to claim 20, wherein the polymeric film comprises a component that provides at least one of: structural integrity in the polymeric film; reduced swelling of the polymeric films when the polymeric film is exposed to hydrocarbon vapors; and enhanced surface adhesion of the polymeric film to a surface of the sensor.

25. The method according to claim 20, wherein the sensor element is a piezoelectric element and the operational characteristic is an oscillation frequency of the piezoelectric element.

26. A method for enhancing detection of a target compound by a sensor, the method comprising:
   providing a sensor having a sensor element that produces a characteristic response when activated;
   disposing a polymeric film on a surface of the sensor element, the polymeric film being able to capture a quantity of the target compound and producing a change in the characteristic response of the sensor element as a result of the capture of the target compound, wherein the polymeric film comprises at least one hardblock component and at least one softblock component; and
   relating the change in the characteristic response of the sensor element to a quantity of the target compound adjacent to the sensor element, wherein the polymeric film comprises at least one polymer selected from polyester elastomer, polyether block polyamides, silicone polyimides, and combinations thereof.

27. A method according to claim 26, wherein the polymeric film comprises polyester elastomer, the polyester elastomer comprising the softblock component and the hardblock component.

28. A method according to claim 27, wherein the softblock component comprises polyoxyalkylene diimide diacids and the hardblock component comprises polyalkylene terephthalate.

29. A method according to claim 26, wherein the polymeric film comprises polyether block polyamides.

30. A method according to claim 29, wherein the polyether block polyamides comprise softblock polyether components and hardblock polyamide (nylon) components.

31. A method according to claim 26, wherein the polymeric film comprises silicone polyimides, the silicone polyimides comprising hardblock and softblock elastomers.

32. A method according to claim 26, wherein the sensor element comprises a quartz crystal microbalance (QCM) sensor that comprises an AT-cut quartz crystal substrate with gold (Au) electrodes.

33. A method according to claim 20, wherein the polymeric film comprises polymers comprising at least one repeating structural units, the repeating structural units being functionalized with groups that enhance selectivity and sensitivity of the sensor to various target compounds.

34. A method according to claim 26, wherein the polymeric film comprises:

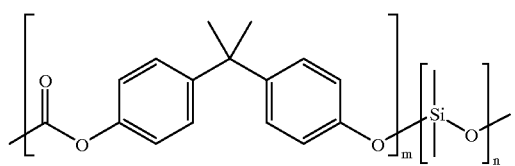

wherein m is in arrange from about 1 to about 4 and n is from about 3 to about 20.

35. A method according to claim 26, wherein the polymeric film comprises:

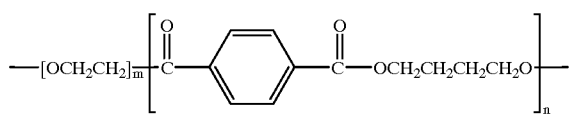

wherein m is in a range from about 10 to about 300 and n is in a range from about 5 to about 300.

36. A method according to claim 36, wherein the polymeric film comprises:

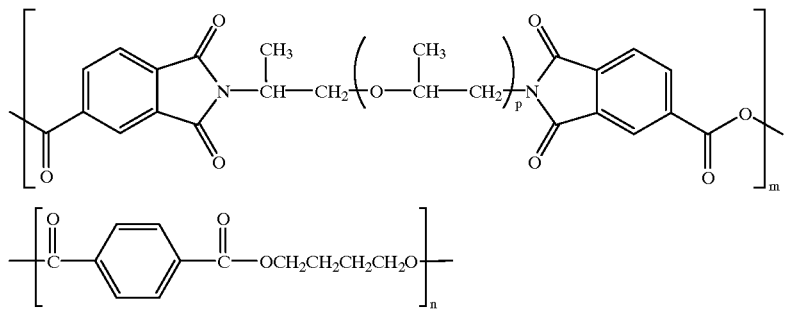
wherein m is in a range from about 1 to about 60, p is in a range from about 10 to 200, and n is in a range from about 5 to about 300.
37. A method according to claim 26, wherein the polymeric film comprises:
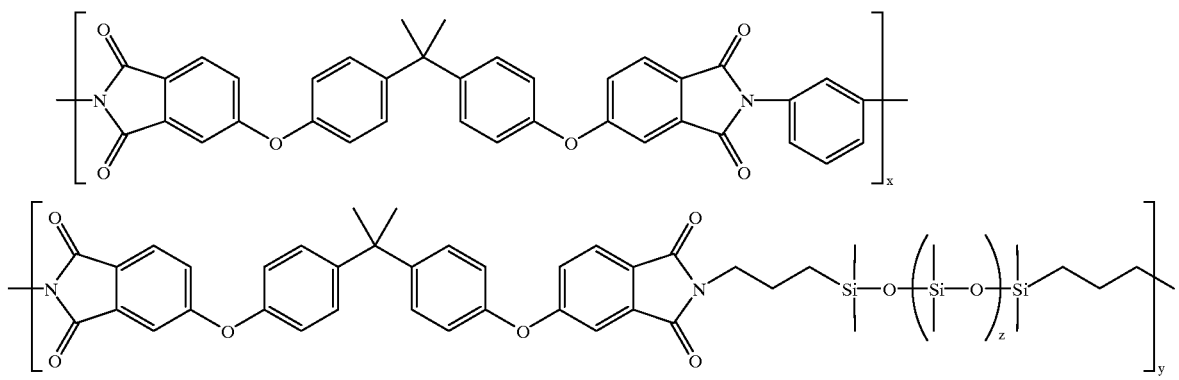
wherein x is in a range from about 1 to about 60, y is in a range from about 40 to 65, and z is in a range from about 3 to about 20.
* * * * *